United States Patent [19]

Auerbach et al.

[11] Patent Number: 5,593,898
[45] Date of Patent: Jan. 14, 1997

[54] DIAGNOSTIC METHOD FOR THE IMMUNOLOGICAL DETERMINATION OF NCAM

[75] Inventors: Bernhard Auerbach; Helmut Peters, both of Marburg, Germany

[73] Assignee: Behringwerke Aktiengesellschaft, Marburg, Germany

[21] Appl. No.: 334,035

[22] Filed: Nov. 2, 1994

Related U.S. Application Data

[63] Continuation of Ser. No. 46,177, Apr. 14, 1993, abandoned.

[30] Foreign Application Priority Data

Apr. 16, 1992 [DE] Germany .......................... 42 12 706.8

[51] Int. Cl.$^6$ .................................................. G01N 33/53
[52] U.S. Cl. ........................ 436/518; 435/7.92; 435/7.93; 435/7.94; 435/962
[58] Field of Search ................................. 435/7.92, 7.93, 435/7.94, 962; 436/518, 818

[56] References Cited

U.S. PATENT DOCUMENTS 5,376,557 12/1994 Schmitt .................................. 435/7.93

FOREIGN PATENT DOCUMENTS

0443599A2 8/1991 European Pat. Off. .

OTHER PUBLICATIONS

"NCAM Biosynthesis In Brain", Nybroe et. al., Neurochem. Int., 12(3):251–262 (1988).

"Expression Of The Embryonal Neural Cell Adhesion Molecule N–Cam In Lung Carcinoma. Diagnostic Usefulness Of Monoclonal Antibody 735 For The Distinction Between Small Cell Lung Cancer And Non–Small Cell Lung Cancer", R. E. Kibbelaar et. al., Journal of Pathology, 159:23–28 (1989).

"NZB Mouse System For Production Of Monoclonal Antibodies To Weak Bacterial Antigens: Isolation Of An IgG Antibody To The Polysaccharide Capsules Of Escherichia coli K1 And Group B Meningococci", Frosch et. al., Proc. Natl., Acad., Sci. USA, 82:1194–1198 (1985).

"Quantification Of The D2–Glycoprotein In Amniotic Fluid And Serum From Pregnancies With Fetal Neural Tube Defects", Ibsen et. al., Journal of Neurochemistry, 41:2 pp. 363–366, (1983).

"An IgG Monoclonal Antibody To Group B Meningococci Cross–Reacts With Developmentally Regulated Polysialic Acid Units Of Glycoproteins In Neural And Extraneural Tissues", Finne et. al., Journal Of Immunology, 138(12):4402–4407 (1987).

"Structure And Biosynthesis Of Surface Polymers Containing Polysialic Acid In Escherichia coli", Rohr et. al., The Journal Of Biological Chemistry, 255(6):2332–2342 (1980).

"Biosynthesis of the Polysialic Acid Capsule In Escherichia coli K1", Weisgerber et. al., The Journal Of Biological Chemistry, 265(3):1578–1587 (1990).

*Primary Examiner*—Toni R. Scheiner
*Assistant Examiner*—Yvonne Eyler
*Attorney, Agent, or Firm*—Finnegan, Henderson, Farabow, Garrett & Dunner, L.L.P.

[57] ABSTRACT

The invention relates to an improved diagnostic method for the immunological determination of NCAM by means of specific binding partners, the one specific binding partner being immobilized on a carrier and the extent of the binding of the analyte to the first specific binding partner being determined by means of a second binding partner which is specific for the analyte and which is labeled either directly or via further binding partners.

7 Claims, 1 Drawing Sheet

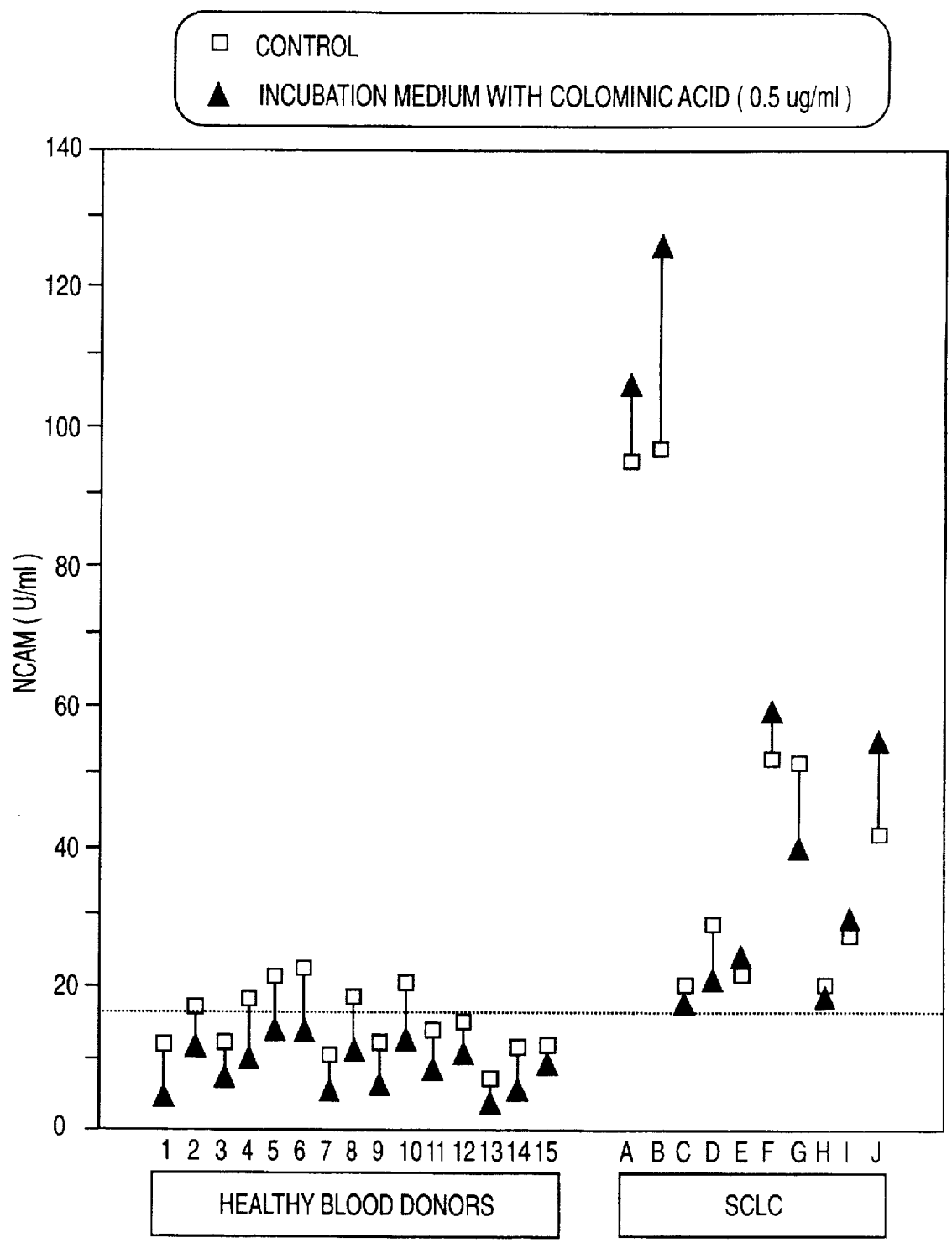

DIAGNOSTIC METHOD FOR THE IMMUNOLOGICAL DETERMINATION OF NCAM

This application is a continuation of application Ser. No. 08/046,177 filed Apr. 14, 1993, now abandoned.

The invention relates to an improved diagnostic method for the immunological determination of one or more analytes by means of specific binding partners, the one specific binding partner being immobilized on a carrier and the extent of the binding of the analyte to the first specific binding partner being determined by means of a second binding partner which is specific for the analyte and which is labeled either directly or via further binding partners.

The "neural cell adhesion molecule" (NCAM) is an intercellular adhesion protein which is expressed in various tissues, in particular neural tissues, of man and also of animals such as, for example, mice, chickens, etc. Three isoforms of different molecular weight have been described, which can also be additionally modified, e.g. by different glycosylation patterns (Nybroe et al., Neurochem. Int., 12, 215–262, 1988). Additionally, NCAM is known from immunohistochemical studies as a tumor-associated antigen of human small cell carcinoma of the lung (SCLC, small cell lung cancer) (Kibbelaar et al., J. Pathol. 159: 23–28, 1989). An immunoassay which, by employing the MAb 735 (Frosch et al., Proc Natl. Acad. Sci. 82: 1194–1198, 1985; Finne et al., J. Immunol. 138: 4402–4407, 1987), specific for α-2,8-linked N-acetylneuraminic acid chains (2,8-NAcN), as a solid-phase antibody in combination with the MAb BW SCLC-1 (ECACC deposit No. 90 022 110) or BW SCLC-2 (ECACC deposit No. 90 022 109), is able to recognize the so-called "embryonic" NCAM isoform, was used to show, surprisingly, that this isoform or an antigen (T-NCAM) defined by the above-described antibodies is present at elevated concentration in the serum of a large number of SCLC patients (EP-A-0,443,599 A2).

Various diagnostic methods are employed for monitoring pregnancy in order to detect fetal malformations at an early stage. In this connection, the immunochemical determination of alpha-fetoprotein (AFP) in amniotic fluid or maternal serum has, inter alia, proved its worth, with elevated concentrations of AFP indicating a defect in the neural tube of the embryo.

Because of false-positive and false-negative findings, it is, however, recommended that additional investigations should be carried out for this indication. Through the work of Ibsen et al. (J. Neurochem. 41: 363–366, 1983) it is known, furthermore, that an elevated concentration of the neural cell adhesion molecule (=D2) in the amniotic fluid is an indication of fetal malformations.

It is, however, also evident from the work of Ibsen et al. that the diagnostic selectivity of their D2 test, i.e. the possibility of distinguishing between healthy and pathological samples, is insufficient when maternal serum, which is more readily available for a first test in pregnancy monitoring, is employed as the sample material.

In addition, it emerged that when the T-NCAM test was converted from a microtiter plate version to a microtube version, the T-NCAM concentration in the sera of healthy blood donors was found to be higher, while the T-NCAM concentration in the sera of tumor patients was determined to be equally high in both tests. The reason for this may be the presence in the samples of a NCAM isoform, with other polysialic acid chains, which crossreacts with the solid phase antibody as well as the tracer/conjugate antibodies and is able to bind more effectively to the microtube solid phase, which is somewhat more reactive immunochemically.

The object of the present invention was therefore to develop an improved T-NCAM test, preferably for the diagnostic investigation of tumors and for monitoring pregnancy, in which the diagnostic selectivity, i.e. the differentiation of pathological and normal samples, is improved.

It emerged, surprisingly, that it was possible to achieve this object by adding to the sample incubation buffer suitable quantities of substances, which (like, e.g., the capsule polysaccharide of E. coli K1) contain α-2,8-linked N-acetylneuraminic acid chains and are specifically bound by the "solid-phase antibody"—e.g. the MAb 735 used in the T-NCAM test—but not by the labeled "tracer-conjugate antibodies"—e.g. the MAbs BW SCLC-1 and -2 used in the T-NCAM test.

The invention therefore relates to a method for the immunological determination of one or more analytes by means of specific binding partners, the one specific binding partner being immobilized on a carrier and the extent of the binding of the analyte to the first specific binding partner being determined by means of a second binding partner which is specific for the analyte and which is labeled either directly or via further binding partners, wherein the reaction at least with one of the specific binding partners takes place in the presence of a suppressor substance which has a high affinity for this specific binding partner but not for the other or for one of the further specific binding partners.

A preferred method of this type is one in which the first specific binding partner is able specifically to bind α-2,8-linked N-acetylneuraminic acid chains, and the second binding partner is specific for the same epitope as the monoclonal antibodies BW SCLC-1 and BW SCLC-2.

The invention further relates to a method of this type wherein the binding partner for which the suppressor substance has an affinity is bound to the solid phase.

The suppressor substance which is used preferably contains α-2,8-linked N-acetylneuraminic acid chains.

It is particularly preferred for the suppressor substance to be composed of components of the capsule polysaccharide from E. coli K1 or type B meningococci or of colominic acid, very particularly preferably of colominic acid.

The suppressor substance is employed at a concentration such that the measurement signal of the test standard is inhibited by not more than 50%, preferably by 20 to 40%, very particularly preferably by about 30%.

In a method of this type, colominic acid is employed at a concentration of 0.01 to 10 µg/ml, preferably of 0.1 to 1 µg/ml.

A possible manner in which these substances act is as follows: the 2,8-NAcN, which are not recognized by the tracer/conjugate antibodies, presumably compete with the T-NCAM molecules and the "crossreacting substance" for the free binding sites of MAb 735. Because of the differential binding of T-NCAM and 2,8-NAcN, e.g. to MAb 735, fewer molecules of the "crossreacting substance", which have lower affinity for the solid-phase antibody than T-NCAM or 2,8-NAcN, are bound, and as a consequence the diagnostic selectivity of the T-NCAM test is ultimately substantially improved. Of decisive importance in the choice of 2,8-NAcN is its ability to bind to the solid-phase antibody. Other glycoproteins which are not bound specifically by MAb 735 but possess an elevated content of sialic acid, such as, e.g., fetuin (Sigma), mucins (Type I-S, Sigma), α1-acid glycoprotein (Behringwerke), or sialic acids (e.g. type VI or type VIII, Sigma) had no effect, even at a concentration of up to 0.1 mg/ml.

The method found for the T-NCAM test can also be employed in an analogous manner for other tests, e.g. for antibody-antigen-antibody "sandwich" immunoassays or for antigen-antibody-antigen "sandwich" immunoassays. In this method, the binding of a crossreacting substance, which is contained in the samples and is recognized by both the specific receptors R1 and R2 employed in the test, to one of the specific receptors R1, itself preferably bound to the solid phase, is prevented by a suppressor substance being added to the sample incubation medium at an appropriate concentration, wherein the suppressor substance competitively inhibits the binding of the crossreacting substance to R1 and does not exhibit a specific binding site for the receptor R2.

An improvement similar to that obtained with the very small quantities of a specific suppressor substance was achieved only with very much higher concentrations of salts such as NaCl or $CaCl_2$. Thus, good results were achieved using a sample incubation buffer with a NaCl concentration of more than 150 to 2,000 mmol/l, particularly in the range from 250 to 1,000 mmol/l. Carbonate buffers with a pH greater than 8.0 (particularly good pH 8–10) have proved to be particularly suitable as buffers, as have Tris buffers or phosphate buffers in the region of pH 6–8.

The diagnostic sensitivity of the T-NCAM test was markedly improved by the above-described measures.

BRIEF DESCRIPTION OF THE FIGURE

The FIGURE shows the serum concentration of T-NCAM in healthy blood donors and patients with small cell carcinoma of the lung (SCLC), determined by a T-NCAM test using a sample incubation medium with and without the addition of 0.5 µg/ml of colominic acid.

The following examples serve to illustrate the invention and do not limit it in any way.

EXAMPLE 1:

Enzyme Immunoassay for Determining T-NCAM in Human Body Fluids

For determining the concentration of T-NCAM, 10 µl of sample material and 100 µl of sample buffer (OSND, Behringwerke) were in each case pipetted into the wells of microtiter plates (Nunc), which had been coated with MAb 735 by a method known to the person skilled in the art, and incubated at 37° C. for one hour.

After three washes with diluted Enzygnost washing buffer (OSEW, Behringwerke), 100 µl of MAb BW SCLC-1-POD or BW SCLC-2-POD-conjugate were in each case added to the individual wells (POD=horseradish peroxidase). The subsequent one-hour incubation step at +37° C. was concluded by a cycle of three washes.

For the 3rd incubation step at room temperature, 100 µl of a buffer/substrate-chromogen solution ($H_2O_2$/TMB; OUVG/OUVF, BW) were next pipetted into each of the wells and the enzyme reaction was terminated after 30 minutes with Enzygnost stop solution (OSFA, BW). Measurement of the extinction of the samples was carried out at 450 nm. The T-NCAM concentrations of the samples were determined quantitatively using an accompanying standard series (unit of measurement: U/ml).

EXAMPLE 2:

Diagnostic Method for Monitoring Pregnancy

The concentration of T-NCAM in samples of amniotic fluid was determined in a manner analogous to the immunochemical method described in Example 1. The AFP concentration was determined using a commercially available test.

Result: Elevated T-NCAM concentrations were measured in amniotic fluid samples when embryonic malformations (e.g. spina bifida or anencephaly) were present (Table 1: Samples 52, 56 and 159). In the case of samples 53 and 139, which have a pathologically elevated AFP concentration, the NCAM concentration correctly lies in the normal range, corresponding to the clinical finding of a healthy embryo. From this it must be concluded that a diagnostic method for determining T-NCAM or NCAM is suitable for pregnancy monitoring (early recognition of embryonic malformations).

TABLE 1

| | T-NCAM concentration in samples of amniotic fluid | | | |
|---|---|---|---|---|
| Sample No. | Week of Pregnancy | AFP (µg/ml) | T-NCAM (U/ml) | Diagnosis |
| 52 | 16 | 188 | 52.7 | anencephalus |
| 56 | 16 | 556 | 57.2 | anencephalus |
| 159 | 20–21 | 76 | 8.9 | spina bifida |
| 53 | 16 | 92 | 1.6 | healthy child |
| 139 | 19 | 200 | 5.1 | healthy child |
| 12 | 16 | 27 | 1.5 | healthy child |
| 13 | 16 | 30 | 1.5 | healthy child |
| 14 | 16 | 24 | 3.7 | healthy child |
| 15 | 16 | 30 | 1.8 | healthy child |
| 16 | 16 | 23 | 3.5 | healthy child |

EXAMPLE 3:

Chemoluminescence Immunoassay for Determining T-NCAM in Human Body Fluids

For determining the concentration of T-NCAM, 20 µl of sample material and 200 µl of sample buffer (e.g. OSND, Behringwerke) were in each case pipetted into polystyrene microtubes (Greiner), which had been coated with MAb 735 by a method known to the person skilled in the art, and incubated at room temperature for one hour with shaking.

After two washes with in each case 2 ml of BeriLux washing buffer (Behringwerke) the individual wells were in each case filled with 200 µl of a solution of MAb BW SCLC-1 or BW SCLC-2 labeled with acridinium-N-acyl-sulfonamide.

The subsequent one-hour incubation step at room temperature and with shaking was concluded by a cycle of three washes.

Subsequently, 300 µl of BeriLux analyzer reagent R1 and R2 (Behringwerke) were in each case added automatically to the microtubes in a luminometer, and the luminogenic measurement signal was measured over a period of 3 seconds. The T-NCAM concentrations of the samples were determined quantitatively using an accompanying standard series (unit of measurement: U/ml).

EXAMPLE 4:

Addition of 2,8-NAcN to the Sample Incubation Buffer to Improve Normal Sera/tumor Sera Discrimination The T-NCAM concentrations of sera from healthy blood donors or of T-NCAM-containing samples, e.g. from patients with small cell carcinoma of the lung, were determined using the immunochemical test method according to Example 3. In this case, various substances were added to the sample incubation medium (OSND, Behringwerke), including compounds such as, for example, a preparation of the E. coli K1 capsule polysaccharide (see also Rohr & Troy, *J. Biol Chem.* 255: 2332–2342, 1980; Weisgerber & Troy, *J. Biol Chem.* 265: 1578–1587, 1990) or colominic acid (Sigma)), which, like the capsule polysaccharide of type B meningococci as well, for example, carry α-2,8-linked N-acetylneuraminic acid chains and are bound specifically by MAb 735 but not by the MAbs BW-SCLC-1 or -2. The amount of 2,8-NAcN added was chosen in such a way that the measurement signal of the test standard was inhibited by between 1 and 50%. Other glycoproteins with an elevated content of sialic acid, such as, for example, fetuin (Sigma), mucins (type I-S, Sigma), α1-acid glycoprotein (Behringwerke) or sialic acids (e.g. type VI or type VIII, Sigma) were employed at a concentration of up to 0.1 mg/ml.

Result: Improved tumor sera/normal sera discrimination was achieved only by the addition of 2,8-NAcN (see also example in Tab. 2 and FIGURE).

TABLE 2

Determination of T-NCAM in normal sera and tumor sera using a sample buffer containing 2,8-NAcN (addition of *E. coli* K1 capsule polysaccharide)

| | Sample buffer | |
|---|---|---|
| | without 2,8-NAcN T-NCAM (U/ml) | plus 2,8-NAcN T-NCAM (U/ml) |
| Tumor sera | | |
| TS 53 | 76.4 | 80.3 |
| TS 608 | 70.9 | 58.4 |
| TS 1058 | 102.0 | 104.7 |
| TS 1350 | 36.7 | 46.5 |
| TS 1462 | 91.9 | 88.9 |
| Normal sera | | |
| NS 1 | 16.6 | 7.9 |
| NS 2 | 21.7 | 11.2 |
| NS 3 | 10.7 | 5.4 |
| NS 4 | 17.6 | 9.6 |
| NS 5 | 14.3 | 6.7 |
| NS 6 | 11.7 | 7.2 |
| NS 7 | 13.5 | 8.2 |
| NS 8 | 9.4 | 5.0 |
| NS 9 | 10.2 | 4.7 |
| NS 10 | 10.4 | 7.6 |
| MEAN: | 13.6 | 7.3 |
| SD: | 3.8 | 2.0 |

EXAMPLE 5:

Addition of Salts/ions to the Sample Incubation Buffer to Improve Normal Sera/tumor Sera Discrimination The T-NCAM concentrations of sera from healthy blood donors or of T-NCAM-containing samples, e.g. from patients with small cell carcinoma of the lung, were determined using the immunochemical test method according to Example 3. In this case, various salts were added to a 50 mM Tris/HCl buffer, pH 7.0, which additionally contained 0.1% of human serum albumin and 0.5% of Tween 20, and this buffer was then used as the sample incubation buffer (results, see Table 3).

TABLE 3

Determination of T-NCAM in normal sera and in samples containing T-NCAM

| | Sample buffer with | | |
|---|---|---|---|
| | 0 mM NaCl | 250 mM NaCl | 500 mM NaCl |
| | (T-NCAM in U/ml) | | |
| T-NCAM samples: | | | |
| A | 62.7 | 78.6 | 73.4 |
| B | 71.6 | 81.6 | 75.9 |
| C | 66.2 | 73.0 | 66.5 |
| D | 63.9 | 77.9 | 78.9 |
| E | 77.6 | 80.8 | 72.5 |
| Normal sera: | | | |
| NS 1 | 18.8 | 12.9 | 9.2 |
| NS 2 | 23.1 | 17.3 | 10.9 |
| NS 3 | 10.9 | 7.0 | 5.6 |
| NS 4 | 17.7 | 13.4 | 10.0 |
| NS 5 | 18.3 | 9.7 | 7.1 |
| NS 6 | 11.1 | 8.4 | 6.8 |
| NS 7 | 14.9 | 11.1 | 7.9 |
| NS 8 | 9.9 | 6.8 | 5.3 |
| NS 9 | 13.7 | 7.8 | 5.1 |
| NS 10 | 15.7 | 10.9 | 6.4 |
| MEAN: | 15.4 | 10.5 | 7.4 |
| SD: | 4.0 | 3.2 | 1.9 |

DESCRIPTION OF THE FIGURE

FIGURE: Serum concentrations of T-NCAM in healthy blood donors and patients with small cell carcinoma of the lung (SCLC), determined by a T-NCAM test using a sample incubation medium (OSND, Behringwerke) with and without (control) the addition of 0.5 μg/ml of colominic acid (Sigma).

We claim:

1. A method for the determination of an analyte, NCAM, in a sample of a biological fluid containing a cross-reacting substance by means of specific binding partners comprising the steps of:

a) binding a first analyte-specific binding partner to a carrier;

b) incubating the bound first analyte-specific binding partner with the sample of the biological fluid to obtain bound analyte;

c) reacting the bound analyte with a second analyte-specific binding partner which second analyte-specific binding partner is labeled with a label either directly or via a binding partner specific for the second analyte-specific binding partner; and d) determining the amount of analyte bound to the bound first analyte-specific binding partner, wherein a measurement signal is derived from said label; wherein either step b) or c) is carried out in the presence of a suppressor substance which specifically binds to said first analyte-specific binding partner or said second analyte-specific binding partner, which is not directly labeled, wherein said suppressor substance has a lower affinity for said first analyte-specific binding partner in step b) than said analyte and said suppressor substance has a higher affinity for said first analyte specific binding partner than said cross-reacting substance or said suppressor substance has a lower affinity for said second analyte-specific binding partner in step c) than said analyte and said suppressor substance has a higher affinity for said second analyte specific binding partner than said cross-reacting substance.

2. The method as claimed in claim 1, wherein the suppressor substance is employed at a concentration such that when a test standard of said NCAM analyte is determined by the method of claim 1, the measurement signal of the test standard is inhibited by not more than 50%.

3. The method as claimed in claim 1, wherein colominic acid is employed at a concentration of 0.01 to 10 µg/ml.

4. The method of claim 1 wherein the first analyte-specific binding partner specifically binds to α-2,8-linked N-acetylneuraminic acid chains and the second analyte-specific binding partner specifically binds to the same epitope as the monoclonal antibodies BW SCLC-1 and BW SCLC-2.

5. The method of claim 1 wherein the suppressor substance specifically binds to the first analyte-specific binding partner bound to the carrier.

6. The method of claim 1 wherein the suppressor substance contains α-2,8-linked N-acetylneuraminic acid chains.

7. The method of claim 1 wherein the suppressor substance is chosen from the group consisting of colominic acid, the capsule polysaccharide from E. coli K 1, and the capsule polysaccharide from B meningococci.

* * * * *